United States Patent
Hochmair et al.

(10) Patent No.: US 7,587,246 B2
(45) Date of Patent: Sep. 8, 2009

(54) IMPLANTABLE DEVICE WITH FLEXIBLE INTERCONNECT TO COIL

(75) Inventors: Erwin Hochmair, Axams (AT); Ingeborg Hochmair, Axams (AT)

(73) Assignee: MED-EL Elektronedizinische Geraete GmbH, Innsbruck (AT)

( * ) Notice: Subject to any disclaimer, the term of this patent is extended or adjusted under 35 U.S.C. 154(b) by 1264 days.

(21) Appl. No.: 10/453,902

(22) Filed: Jun. 3, 2003

(65) Prior Publication Data

US 2003/0229381 A1 Dec. 11, 2003

Related U.S. Application Data

(60) Provisional application No. 60/385,313, filed on Jun. 3, 2002.

(51) Int. Cl.
*A61N 1/00* (2006.01)
(52) U.S. Cl. .................................................. 607/60
(58) Field of Classification Search ................ 607/33, 607/55–61, 137; 600/25; 523/427
See application file for complete search history.

(56) References Cited

U.S. PATENT DOCUMENTS

| | | | | |
|---|---|---|---|---|
| 4,292,213 A | * | 9/1981 | Elliott et al. ............... | 523/427 |
| 4,612,915 A | * | 9/1986 | Hough et al. ............... | 600/25 |
| 5,549,658 A | * | 8/1996 | Shannon et al. ............ | 607/57 |
| 5,613,935 A | | 3/1997 | Jarvik ........................ | 600/16 |
| 6,067,474 A | | 5/2000 | Schulman et al. .......... | 607/57 |
| 6,272,382 B1 | | 8/2001 | Faltys et al. ................ | 607/57 |
| 6,308,101 B1 | | 10/2001 | Faltys et al. ................ | 607/57 |
| 6,358,281 B1 | | 3/2002 | Berrang et al. ............. | 623/10 |

FOREIGN PATENT DOCUMENTS

WO WO 01/74447 A2 10/2001

OTHER PUBLICATIONS

International Search Report of Sep. 26, 2003.

* cited by examiner

*Primary Examiner*—George Manuel
(74) *Attorney, Agent, or Firm*—Sunstein Kann Murphy & Timbers LLP

(57) ABSTRACT

An implant for implantation into a person. The implant includes a hermetically sealed housing enclosing electrical circuitry. A first coil is flexibly coupled to the housing such that the first coil is external to the housing and capable of being repositioned relative to the housing. The first coil is capable, after being implanted in the person, of being arranged adjacent a second coil of a remote device, such that first coil and the second coil are inductively coupled. The first coil may be adapted to receive at least one of a power signal and a data signal from a remote source.

35 Claims, 2 Drawing Sheets

IMPLANTABLE DEVICE WITH FLEXIBLE INTERCONNECT TO COIL

PRIORITY

This application claims priority from U.S. Provisional Application No. 60/385,313, filed Jun. 3, 2002, entitled "Implantable Device with Flexible Interconnect to Coil", the disclosure of which is incorporated herein by reference.

TECHNICAL FIELD

The present invention relates to an implantable device, such as a cochlear implant, that has a flexible interconnect between the main electronics package and a coil arrangement.

BACKGROUND

Hermetically encapsulated electronic devices for long term implantation generally use one or more coils being inductively coupled to external coils to either provide one or two-way communication with external devices and/or provide the power supply for the internal electronics (e.g. when the internal battery fails), or for recharging internal batteries. An example are cochlear implants.

Conventional cochlear implants either use ceramic cases or metal cases for the hermetic encapsulation of the electronics. When using ceramic packages, the coil can easily be placed within the package. For safety reasons metal packages are a better choice when employing internal rechargeable or non-rechargeable batteries. This requires the placement of the coil(s) outside the hermetic metal case. In present devices, this coil is connected to the case by a mechanically rigid construction, thus making the total implant rather clumsy and difficult to place, especially with small children.

Possible problems with a rigid connection that results in a fixed angle between the coil and the electronic housing include frequent movement in the area of interconnection through external pressure to the skin due to, for example, glasses, helmet, headphones, combs and/or pressure from overlying muscle tissue. Curvature changes in the skull as a child ages aggravates these problems, and can lead to wire breakages, skin breakdown over the implant, and fluid accumulation beneath the implant.

SUMMARY OF THE INVENTION

In a first embodiment of the invention, an implant for implantation into a person is presented. The implant includes a housing. A first coil is flexibly coupled to the housing such that the first coil is external to the housing and capable of being repositioned relative to the housing.

In related embodiments of the invention, the first coil may be capable, after being implanted in the person, of being arranged adjacent a second coil of a remote device, such that first coil and the second coil are inductively coupled. The first coil may be adapted to receive a power signal from the remote device. The implant may include a battery, which may be rechargeable based on the received power signal. The first coil may be adapted to receive data signals from the remote device.

In further related embodiments of the invention, the first coil may be electrically coupled to electrical circuitry enclosed within the housing. One or more electronic components may be enclosed in the housing, such as a transmitter, a receiver, a signal processor, an actuator, a battery and a sensor. The first coil may be flexibly coupled to the housing by an electronic interconnect, which may be, for example, a cable. The cable may include one or more wires, wherein the wire may be a litz wire, a multistrand wire, a singlestrand wire, a coiled wire, and a serrated wire. The wire may be made of PtIr, Pt, Au, Ag, Cu, Ta and/or Nb. The housing may be electrically conductive, or made of a ceramic material. Insulating material may, such as silicone, Teflon, and parylene cover at least one portion of the coil. The implant may be removably coupled to the housing. The coil may be coupled to the housing via a hermetic feedthrough in the housing.

In still further related embodiments of the invention, the implant is a cochlear implant. The housing may be coupled to an element positioned external to the housing, the element being one of an electrode, a sensor, and an actuator. At least one fastener may be used to attach the coil and/or the housing to the skull. The fastener may be a bone screw, a hook, sutures, or a clamp.

In another embodiment of the invention, a method of providing an implantable system includes providing electrical circuitry into an implantable, hermetically sealed housing. An antenna coil is flexibly attached to the housing such that the coil is external to the housing and capable of being repositioned relative to the housing, the antenna coil adapted to receive at least one of a power signal and a data signal from a remote source.

In related embodiments of the invention, the coil may be electrically coupled to the housing so that the at least one of the power signal and the data signal can be shared between the electrical circuitry contained in the housing. Flexibly attaching the coil to the housing may include providing a cable to electrically couple the antenna coil to the housing. A rechargeable battery may be enclosed in the housing, the rechargeable battery capable of being recharged based on the power signal. An element may be externally attached to the housing, such as an electrode, sensor, and an actuator.

In further related embodiments of the invention, a means for delivering stimulating pulses to body tissue may be attached to the housing. The means for delivering the stimulation pulses may include at least one electrode.

In still further related embodiments of the invention, the housing and the coil may be implanted into a person. A groove may be milled in a bone, such as the skull, into which the flexible interconnect is placed. Additionally, a first area and a second area may be milled in the bone, for placement of the coil and the housing. The coil and/or housing may be fastened to the skull, using, without limitation, bone screws, sutures, hooks or clamps.

BRIEF DESCRIPTION OF THE DRAWINGS

The foregoing features of the invention will be more readily understood by reference to the following detailed description, taken with reference to the accompanying drawings, in which:

FIG. 2 is a schematic diagram of an implantable device that includes stimulating electrodes, in accordance with one embodiment of the invention; and.

DETAILED DESCRIPTION

In illustrative embodiments of the invention, a system and method for an implantable device includes a flexible interconnect between the implant's housing and a coil. The implant may be, without limitation, a cochlear implant, a brain stem implant, or a middle ear implant. The flexible interconnect allows the coil to be placed at various locations relative to the housing and at an appropriate angle conforming, for example, to a person's skull. The same implant may be used for implantation at right or left sides (e.g. right and left ears) of a person, which typically is not possible with traditional implants. Breakdown of the implant into flexibly connected smaller parts may be particularly advantageous when placing the implantable device in small children, where implantation of a large device is often impractical. Use of a flexible interconnect allows for growth-induced bone curvature, angle and position changes (e.g. skull growth). Details of illustrative embodiments are discussed below.

Figure 1:
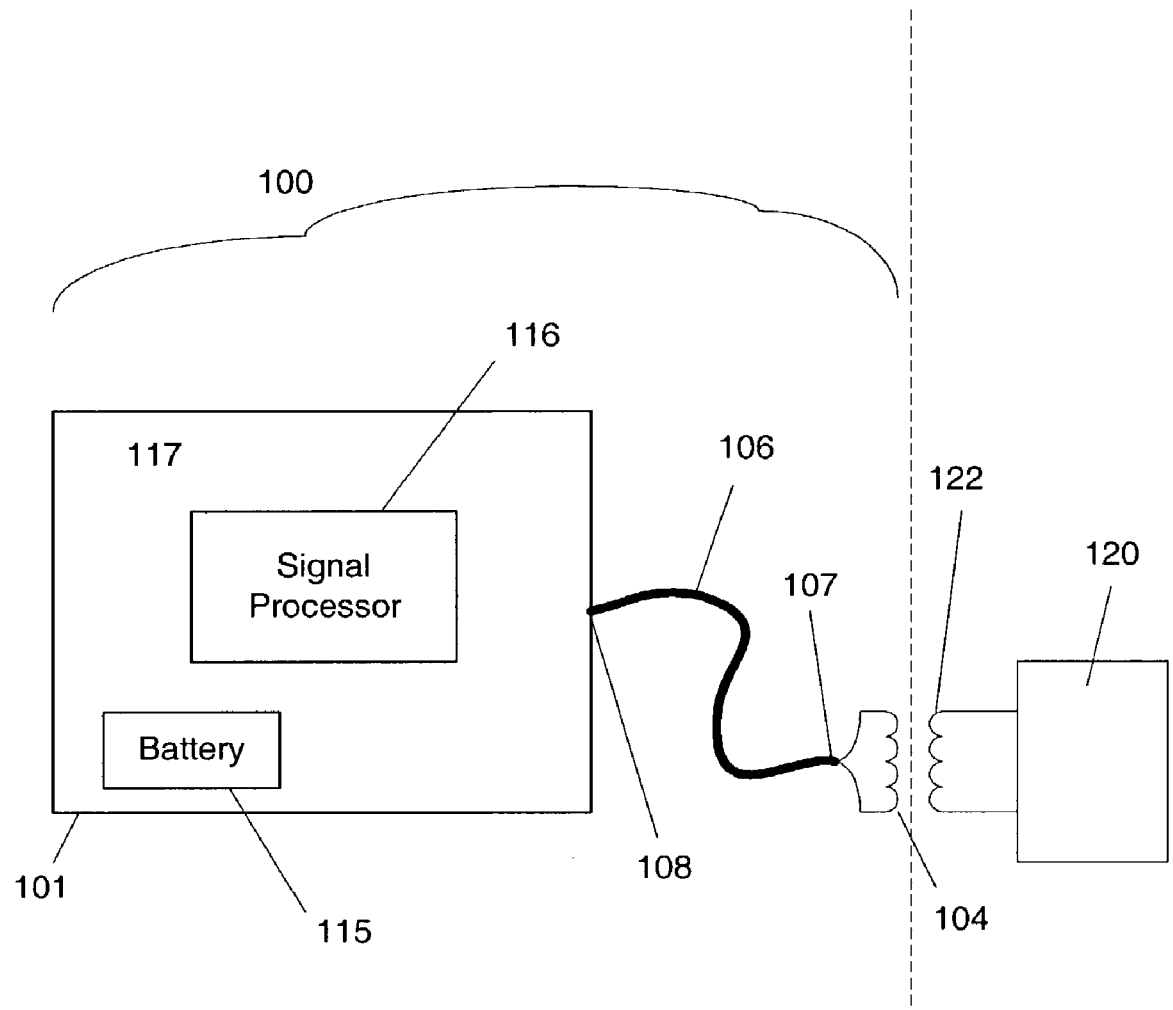
FIG. 1 is a schematic diagram of an implantable device, in accordance with one embodiment of the invention.

In accordance with one embodiment of the invention, FIG. 1 shows an implantable device 100 having a housing 101. The housing 101 may be made of, without limitation, a ceramic or an electrically conductive material, such as a metal. Typically, housing 101 is hermetic so as to prevent corrosion and/or leakage of material into or out of the body of the housing 101. Various electronic circuitry 117 is commonly placed within the housing 101, dependent on implant functionality. Examples of electronic circuitry 117 include, without limitation, a battery 115, a sensor, an actuator, and/or a signal processor 116.

An antenna coil 104 is attached to the housing 101 via a flexible interconnect 106. Flexible interconnect 106 allows the antenna coil 104 to be repositioned with respect to housing 101. Antenna coil 103 may be encapsulated/insulated using materials such as silicone, polytetrafluoroethylene (available from E. I. du Pont de Nemours and Company ("Dupont") Wilmington, Del., under the trademark TEFLON), or parylene.

The flexible interconnect 106 may be, without limitation, an electrical interconnect such as a cable. The cable includes one or more wires. The wire may be, for example, a litz wire, a multistrand wire, a singlestrand wire, a coiled wire, and/or a serrated wire. Wire material may be, without limitation, Platinum Ridium (PtIr), Platinum (Pt), Gold (Au), Silver (Ag), Copper (Cu), Tantalum (Ta) and/or Niobium (Nb).

The flexible interconnect 106 may attach at a first end 107 to the coil 104, and at a second end 108 to the housing 101. The second end 108 of the flexible interconnect 106 may pass, for example, through a hermetically sealed connection of housing 101, and further be electronically coupled to one or more electronic components within the housing 101. The first end 107 and/or the second end 108 of the flexible interconnect 106 may be removably coupled to the coil 104 and housing 101, respectively, via, without limitation, a pin and socket type connection or other means known in the art. In other embodiments, ends 107 and/or 108 may be soldered or welded to the coil 104 and electronic components/connections on or within housing 101, respectively. In various embodiments, the coil 104 and flexible interconnect 106 include a continuous wire.

The coil 104, when implanted in a person, may be arranged adjacent a second coil 122 of a remote device 120 such that power signals and/or data signals can be transmitted between the two coils 104 and 122 via inductive coupling. The remote device 120 may be positioned outside the body so that coils 104 and 122 form a transformer that allows signals to be transculateously transferred. Signals transferred to coil 104 are passed to the electronic circuitry 117 within housing 101 via the flexible interconnect 106. Communication between the remote device 120 and implant 100 may be unidirectional or bidirectional.

Power signals transferred to the coil 104 and further passed to the electronic components 117 within the housing may be used, for example, to recharge the battery 115 or otherwise provide power to the implant 100. Data signals transferred to the coil may be, without limitation, representative of acoustic signals that are detected by a microphone in a speech processor of a cochlear implant.

Figure 2:
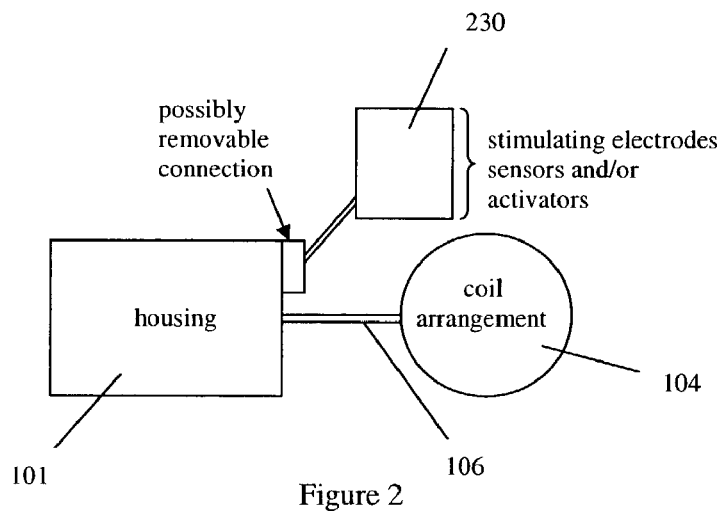

As shown in FIG. 2, implant 100 may include an element 230, other than coil 104, that is attached to housing 101. The element 230 may be, without limitation, stimulating electrodes, sensors, and/or activators that are coupled, possibly via a removable connection, to the housing 101. The element(s) 230 may also be flexibly attached to the housing 101 and repositionable relative to the housing 101.

Figure 3:
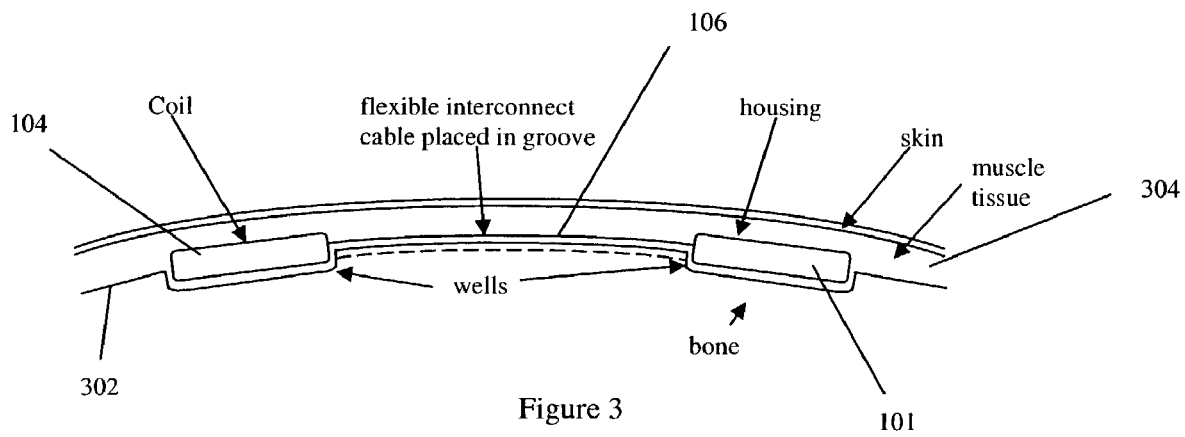
FIG. 3 is a schematic diagram of an implantable device fixed to the skull, in accordance with one embodiment of the invention.

FIG. 3 is a schematic diagram of an implantable device 101 fixed to a bone, such as the skull 302, in accordance with one embodiment of the invention. Flexible interconnect 106 is placed in a groove in the skull 302, where it is protected from mechanical stress. The implant housing 101 is typically placed and fixed in a milled well in the skull 302 (in the temporal bone in the case of a cochlear implant). Coil 104 may also be placed and fixed in a milled well in the skull 302, since it is typically not sufficient to just slide the coil 104 under the muscle tissue 304 or the periost covering the skull 302. The fixation may be done by placing the housing 101 or coil 104 in a milled out well, where it can be held in place by, without limitation, sutures, bone screws, little hooks and/or or clamps mounted at the side facing the bone. The housing 101 and/or coil 104 will generally be securely anchored to the skull 302 within a few months postoperatively.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. An implant for implantation into a person comprising:
   a housing;
   an electrode stimulating element flexibly attached to the housing; and
   a first coil flexibly coupled to the housing such that the first coil is external to the housing and capable of being repositioned relative to the housing.

2. The implant system according to claim 1, wherein the first coil is capable, after being implanted in the person, of being arranged adjacent a second coil of a remote device, such that first coil and the second coil are inductively coupled.

3. The implant according to claim 2, wherein the first coil is adapted to receive a power signal from the remote device.

4. The implant according to claim 3, wherein the implant further includes a battery, the battery capable of being recharged based on the power signal.

5. The implant according to claim 2, wherein the first coil is adapted to receive data signals from the remote device.

6. The implant according to claim 1, wherein the first coil is electrically coupled to electrical circuitry enclosed within the housing.

7. The implant according to claim 1, wherein one or more electronic components is enclosed in the housing, the one or more electronic components including at least one of a transmitter, a receiver, a signal processor, an actuator, a battery and a sensor.

8. The implant according to claim 1, wherein the first coil is flexibly coupled to the housing by an electronic interconnect.

9. The implant according to claim 8, wherein the electronic interconnect is a cable.

10. The implant according to claim 9, wherein the cable includes one or more wires.

11. The implant according to claim 10, wherein the one or more wires includes at least one of a litz wire, a multi-strand wire, a single-strand wire, a coiled wire, and a serrated wire.

12. The implant according to claim 10, wherein the one or more wires may be made of at least one material from the group of materials consisting of platinum iridium, platinum, gold, silver, copper, tantalum and niobium.

13. The implant according to claim 1, wherein the housing is electrically conductive.

14. The implant according to claim 1, wherein the housing is made of a ceramic material.

15. The implant according to claim 1, further comprising insulating material covering at least one portion of the coil.

16. The implant according to claim 1, wherein the insulating material is one of silicone, polytetrafluoroethylene, and parylene.

17. The implant according to claim 1, wherein the coil is removably coupled to the housing.

18. The implant according to claim 1, wherein the coil is coupled to the housing via a hermetic feedthrough in the housing.

19. The implant according to claim 1, wherein the implant is a cochlear implant.

20. The implant according to claim 1, wherein the housing is coupled to an element positioned external to the housing, the element being one of an electrode, a sensor, and an actuator.

21. The implant according to claim 1, further comprising at least one fastener for attaching the coil and/or the housing to the skull.

22. The implant according to claim 21, wherein the at least one fastener is one of a bone screw, a hook, a suture, and a clamp.

23. A method of providing an implantable system comprising:
   providing electrical circuitry into an implantable, hermetically sealed housing;
   flexibly attaching an electrode stimulating element to the housing; and
   flexibly attaching an antenna coil to the housing such that the coil is external to the housing and capable of being repositioned relative to the housing, the antenna coil adapted to receive at least one of a power signal and a data signal from a remote source.

24. The method according to claim 23, wherein flexibly attaching the coil to the housing includes electrically coupling the antenna coil to the housing so that the at least one of the power signal and the data signal can be shared between the electrical circuitry contained in the housing.

25. The method according to claim 24, further comprising:
   placing a rechargeable battery in the housing, the rechargeable battery capable of being recharged based on the power signal.

26. The method according to claim 25, wherein the means for delivering includes at least one electrode.

27. The method according to claim 23, wherein flexibly attaching the coil to the housing includes providing a cable to electrically couple the antenna coil to the housing.

28. The method according to claim 23, further comprising attaching an element to the housing, the element positioned external to the housing, the element being one of an electrode, a sensor, and an actuator.

29. The method according to claim 23, further comprising attaching a means for delivering stimulating pulses to body tissue.

30. The method according to claim 23, further comprising implanting the housing and the coil into a person.

31. The method according to claim 30, wherein flexibly attaching the coil to the housing includes providing a cable to electrically couple the antenna coil to the housing, and wherein the implanting includes:
   milling a groove in a bone; and
   placing the cable in the groove.

32. The method according to claim 31, wherein the implanting includes:
   milling a first area of the bone; and
   placing the housing in the first area.

33. The method according to claim 32, wherein the implanting includes:
   milling a second area of the bone; and
   placing the coil in the second area.

34. The method according to claim 33, wherein the implanting includes:
   fastening the coil to the first area; and
   fastening the housing to the second area.

35. The method according to claim 23, wherein flexibly attaching the antenna coil to the housing includes coupling the antennae to the housing via a cable.

* * * * *

UNITED STATES PATENT AND TRADEMARK OFFICE
CERTIFICATE OF CORRECTION

PATENT NO. : 7,587,246 B2 Page 1 of 1
APPLICATION NO. : 10/453902
DATED : September 8, 2009
INVENTOR(S) : Erwin S. Hochmair et al.

It is certified that error appears in the above-identified patent and that said Letters Patent is hereby corrected as shown below:

In Col. 2, line 8
replace "The implant may"
with "The coil may"

In Col. 3, line 40
replace "Platinum Ridium"
with "Platinum Iridium"

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,587,246 B2
APPLICATION NO. : 10/453902
DATED : September 8, 2009
INVENTOR(S) : Hochmair et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1434 days.

Signed and Sealed this

Twenty-first Day of September, 2010

David J. Kappos
*Director of the United States Patent and Trademark Office*